United States Patent
Kaftan et al.

(10) Patent No.: US 9,220,438 B2
(45) Date of Patent: Dec. 29, 2015

(54) METHOD FOR COMBINING MULTIPLE IMAGE DATA SETS INTO ONE MULTI-FUSED IMAGE

(71) Applicants: Jens Kaftan, Oxford (GB); Matthew David Kelly, Botley (GB)

(72) Inventors: Jens Kaftan, Oxford (GB); Matthew David Kelly, Botley (GB)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 14/185,437

(22) Filed: Feb. 20, 2014

(65) Prior Publication Data
US 2014/0233822 A1    Aug. 21, 2014

(30) Foreign Application Priority Data
Feb. 20, 2013 (GB) .................................. 1302986.3

(51) Int. Cl.
*A61B 5/055* (2006.01)
*A61B 5/00* (2006.01)

(52) U.S. Cl.
CPC .............. *A61B 5/055* (2013.01); *A61B 5/0035* (2013.01)

(58) Field of Classification Search
CPC .................................. A61B 5/00; G06T 11/60
USPC ........ 382/128, 131; 600/427, 436; 378/4, 131
See application file for complete search history.

(56) References Cited

U.S. PATENT DOCUMENTS

| | | | |
|---|---|---|---|
| 6,807,247 B2* | 10/2004 | Krishnan et al. | 378/4 |
| 2003/0174872 A1 | 9/2003 | Chalana et al. | |
| 2003/0216631 A1 | 11/2003 | Bloch et al. | |
| 2004/0030246 A1* | 2/2004 | Townsend et al. | 600/427 |
| 2004/0096088 A1* | 5/2004 | Kohle | 382/128 |
| 2006/0004275 A1* | 1/2006 | Vija et al. | 600/407 |
| 2006/0242143 A1* | 10/2006 | Esham et al. | 707/6 |
| 2008/0008366 A1 | 1/2008 | Desh et al. | |
| 2008/0009707 A1 | 1/2008 | Theriault | |
| 2009/0087061 A1* | 4/2009 | Xu et al. | 382/131 |
| 2009/0097726 A1 | 4/2009 | Rusko et al. | |
| 2009/0129641 A1* | 5/2009 | Zhou | 382/128 |
| 2010/0014730 A1* | 1/2010 | Hahn et al. | 382/131 |
| 2010/0067768 A1* | 3/2010 | Ionasec et al. | 382/131 |
| 2010/0316272 A1* | 12/2010 | Kadir et al. | 382/128 |
| 2012/0177258 A1* | 7/2012 | Hakl et al. | 382/128 |

OTHER PUBLICATIONS

Lin et al., "Prospective comparison of combined 18F-FDG and 18F-NaF PET/CT vs. 18F-FDG PET/CT imaging for detection of malignancy," Eur J Nucl Med Mol Imaging, vol. 39 (2012) pp. 262-270.

(Continued)

*Primary Examiner* — Samir Ahmed
(74) *Attorney, Agent, or Firm* — Schiff Hardin LLP

(57) ABSTRACT

In a method and an apparatus to visualize nuclear medicine data from different modalities in a single image, image data sets acquired with different modalities are aligned with a data set representing corresponding anatomical data. The image data in each data set are segmented into separate regions, representing respective structures of interest, with reference to a segmentation derived from anatomical data. For each region, a corresponding segment of image data is selected from a selected image data set. The selected segments of the image data set are combined to generate a multi-fused image of the regions, by applying spatially dependent look-up tables to the multiple image data sets, thereby to determine whether each data set is hidden or displayed in each region.

11 Claims, 3 Drawing Sheets

(56) References Cited

OTHER PUBLICATIONS

Hetzel et al., "F-18 NaF PET for Detection of Bone Metastases in Lung Cancer: Accuracy, Cost-Effectiveness, and Impact on Patient Management," Journal of Bone and Mineral Research vol. 18, (2003) pp. 2206-2214.

Kohlberger, et al. "Automatic Multi-Organ Segmentation Using Learning-based Segmentation and Level Set Optimization", MICCAI (2012).

* cited by examiner

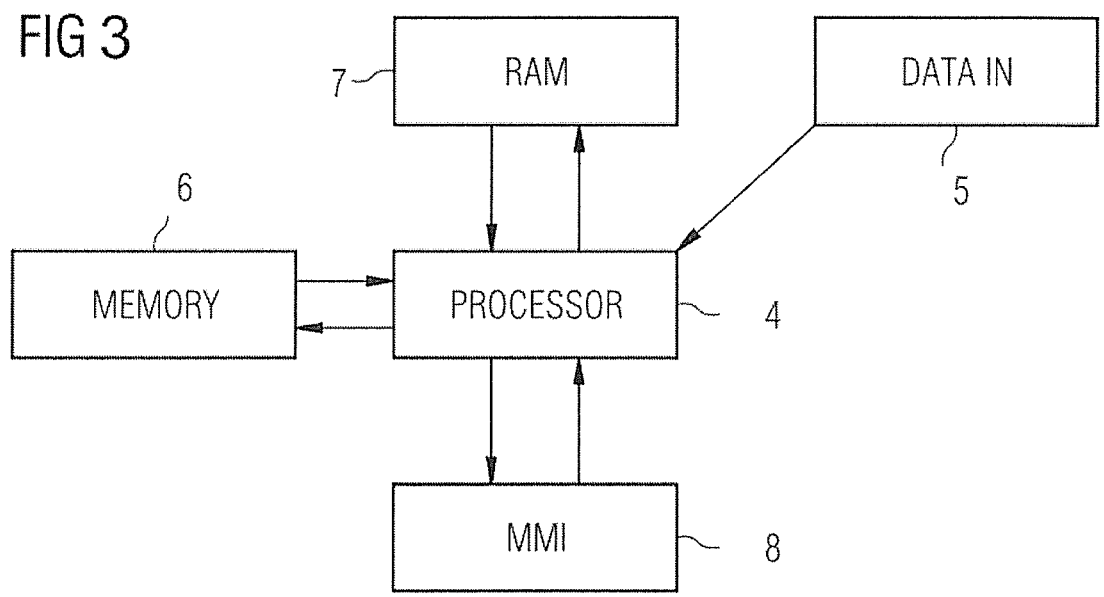

METHOD FOR COMBINING MULTIPLE IMAGE DATA SETS INTO ONE MULTI-FUSED IMAGE

BACKGROUND OF THE INVENTION

1. Field of the Invention

The present invention concerns a method and an apparatus to visualize nuclear medicine data from different modalities, in a single image.

2. Description of the Prior Art

The following definitions, acronyms and abbreviations are used herein:

PET Positron emission tomography
SPECT Single-photon emission tomography
NaF Sodium fluoride
NM Nuclear medicine
MIP Maximum intensity projection
CT Computed tomography
FDG Flodeoxyglucose
MPR Multi-planar reformatting/reconstruction/rendering
MRI Magnetic resonance imaging
RGBA Color representation as red/green/blue and alpha (opacity)
LUT Look-up table: in this context, a LUT contains the transformation from observed values (here, uptake values) to visualized pixel/voxel values, often encoded as RGBA.
VOI Volume of Interest
HSV Hue Saturation Value With the clinical availability of more and more nuclear imaging tracers, a detailed examination of a patient may combine information collected from image data acquired with more than one radioisotope. For instance a combination of $^{18}$F-FDG and $^{18}$F—NaF PET/CT increases the sensitivity for detection of osseous lesions compared to $^{18}$F-FDG PET/CT alone, independent of whether both scans were performed as separate studies or as a single study with simultaneous tracer injection, as described in Lin et al., "Prospective comparison of combined $^{18}$F-FDG and $^{18}$F—NaF PET/CT vs. $^{18}$F-FDG PET/CT imaging for detection of malignancy," Eur J Nucl Med Mol Imaging 2012, 39, pp. 262-270. While in this example $^{18}$F—NaF PET/CT provides particular advantages in detecting bone metastasis (See Hetzel et al., "F-18 NaF PET for Detection of Bone Metastases in Lung Cancer: Accuracy, Cost-Effectiveness, and Impact on Patient Management," Journal of Bone and Mineral Research 2003, 18(12), pp. 2206-2214), it can be expected that other tracers will prove themselves useful for detecting pathologies in other structures/organs. Hence, a combination of more than one tracer will, for certain medical questions, reveal more information to the reading physician than a single tracer alone can.

The increasing amount of information for the reading physician makes it at the same time more and more difficult to get a fast overview of the patient's condition and to focus on diagnostically relevant organs and structures. This is particularly true if more than one scan with multiple radioisotopes has been acquired.

Currently multiple studies with different tracers are typically reviewed individually or side-by-side. For this purpose, a LUT, which may be a color LUT, is often applied to the functional data and the result is visualized as overlay on the corresponding anatomical data, if available. In the following, such visualization is referred to as fused imaging, or fusion. Furthermore, 3D visualizations may be rendered using, for instance, a maximum-intensity-projection (MIP) to display an overview of the NM data.

In the case of multiple-tracers being combined in one study, no conventional dedicated rendering techniques are currently known.

That is, similar to above, one LUT is applied for fused imaging or to generate a MIP. In that case the correlation between each tracer and the observed uptake is lost. Note that cases where uptake can be associated to the individual tracer, e.g., SPECT imaging of tracers emitting photons of different energies, can be regarded as the first use-case that includes multiple studies.

SUMMARY OF THE INVENTION

The present invention accordingly provides apparatus and methods to visualize NM data, e.g., acquired with PET/CT, SPECT/CT, SPECT/MR or PET/MR scanners, using multiple tracers in a single image.

The present invention accordingly provides methods wherein multiple image data sets are combined into one multi-fused image, as defined in the appended claims.

BRIEF DESCRIPTION OF THE DRAWINGS

FIG. 3 schematically shows an apparatus according to an embodiment of the invention.

DESCRIPTION OF THE PREFERRED EMBODIMENTS

The present invention provides systems and methods to visualize NM data from different modalities in a single image. The different modalities may include images from PET/CT, SPECT/CT, SPECT/MR or PET/MR scanners, using multiple tracers.

Tracer uptake values from the scans and acquired with multiple tracers are displayed in a meaningful way, allowing a user to get an overview of a patient in a single image dataset.

The present invention may be applied regardless of whether the different tracers were imaged separately or simultaneously.

The present provides organ-specific LUTs for multi-tracer studies. That is, for each segmented organ or structure (see T. Kohlberger, J. Zhang, M. Sofka, et al. "Automatic Multi-Organ Segmentation Using Learning-based Segmentation and Level Set Optimization", MICCAI 2012, Springer LNCS.) a selected tracer can be visualized using an appropriate LUT and combined into one single image. In other words, different color maps are spatially applied depending on a segmentation result.

Figure 1A:
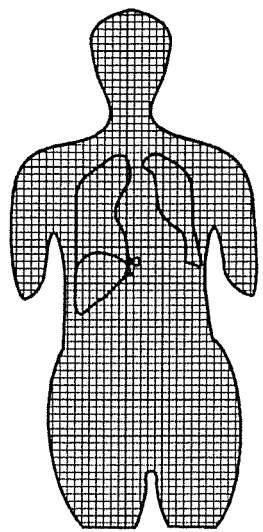
FIGS. 1A-1C represent images of a patient according to respective modalities.
Figure 1B:
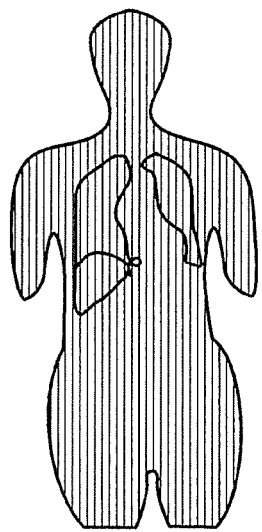
Figure 1C:
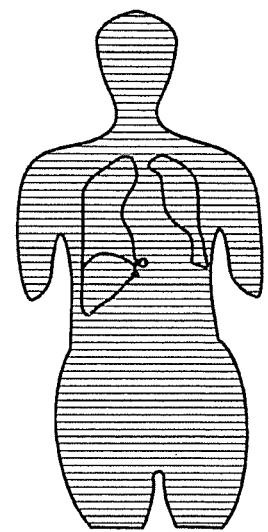

FIGS. 1A-1D: One patient has been consecutively scanned with 3 different NM tracers. FIG. 1A indicates a fused visualization of anatomical information (body outline) superimposed by a color-coded overlay (checked pattern) of tracer A. FIGS. 1B and 1C show similar fused visualizations using tracer B (vertical stripes) and tracer C (horizontal stripes), respectively. All overlays are combined into one multi-fused image, shown in FIG. 1D, by spatially applying different LUTs for respective tracers A-C utilizing anatomical segmentation results of lung and liver.

The example illustrated in FIGS. 1A-1D will be used for explanation. FIGS. 1A-1C represent image data acquired from three respective NM studies where different tracers have been used.

The acquired data and all associated volumes are registered to each other, for example using a registration algorithm or the scanner alignment.

In this example, tracer A is used in the acquisition of the image of FIG. 1A. It has high sensitivity for detecting liver lesions. Tracer B, used in the acquisition of the image of FIG. 1B, is advantageous for imaging the lung. Tracer C, used in the acquisition of the image of FIG. 1C, can be considered as an "all-rounder", and is reasonably effective at detecting lesions in most parts of the body.

A segmentation of the lungs and liver is made available from associated anatomical data. Accordingly, regions of the images which correspond to each segment of the data can be identified and isolated. In a method according to the present invention, a composite image, as shown in FIG. 1D, may be produced using identified segments from each of the images 1A-1C, each segment being chosen from the image which is expected to produce the best definition for that segment based on the tracer(s) used in the acquisition of that image.

In the present example, a liver LUT would be used that selects the liver image data acquired using tracer A (FIG. 1A) but hides liver image data acquired using tracers B & C (FIGS. 1B and 1C). A lung LUT would be used that selects the lung image data acquired using tracer B (FIG. 1B) but hides lung image data acquired using tracers A & C (FIGS. 1A and 1C). For the remaining part of the body, a LUT would be used that selects the image data acquired using tracer C (FIG. 1C) but hides image data acquired using tracers A & B (FIGS. 1A and 1B).

Figure 1D:
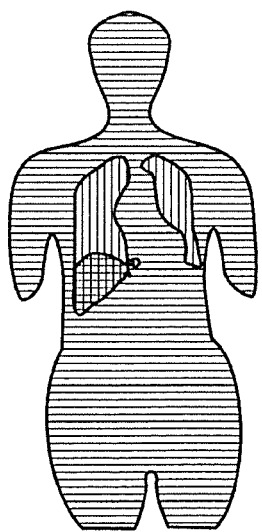
FIG. 1D represents a combined image assembled from respective regions of interest in different respective modalities, according to an embodiment of the invention.

The result, illustrated in FIG. 1D, is an image generated by using an organ-specific LUT that spatially highlights different tracers for different organs. In the following description, such an image will be referred to as multi-fused image.

Note that the utilized LUTs can be chosen in different ways. In one example, the utilized LUTs can be designed such that uptake from different tracers can be easily visually differentiated, e.g., using different color schemes for each tracer. In another example, the utilized LUTs can be adjusted to compensate for the naturally varying dynamic range of each tracer such that the resulting multi-fused image looks similar to a conventional single-tracer image.

As a consequence, for each organ or structure, the image data generated from the tracer with the optimal clinical sensitivity is shown. This allows a user to get a detailed overview of the patient's condition, and may assist the user in deciding whether to examine each individual image separately. Preferably, each individual image can be visualized in parallel to the multi-fused image. This may be achieved by providing a multi-image display on a monitor, as shown in FIG. 2.

Figure 2:
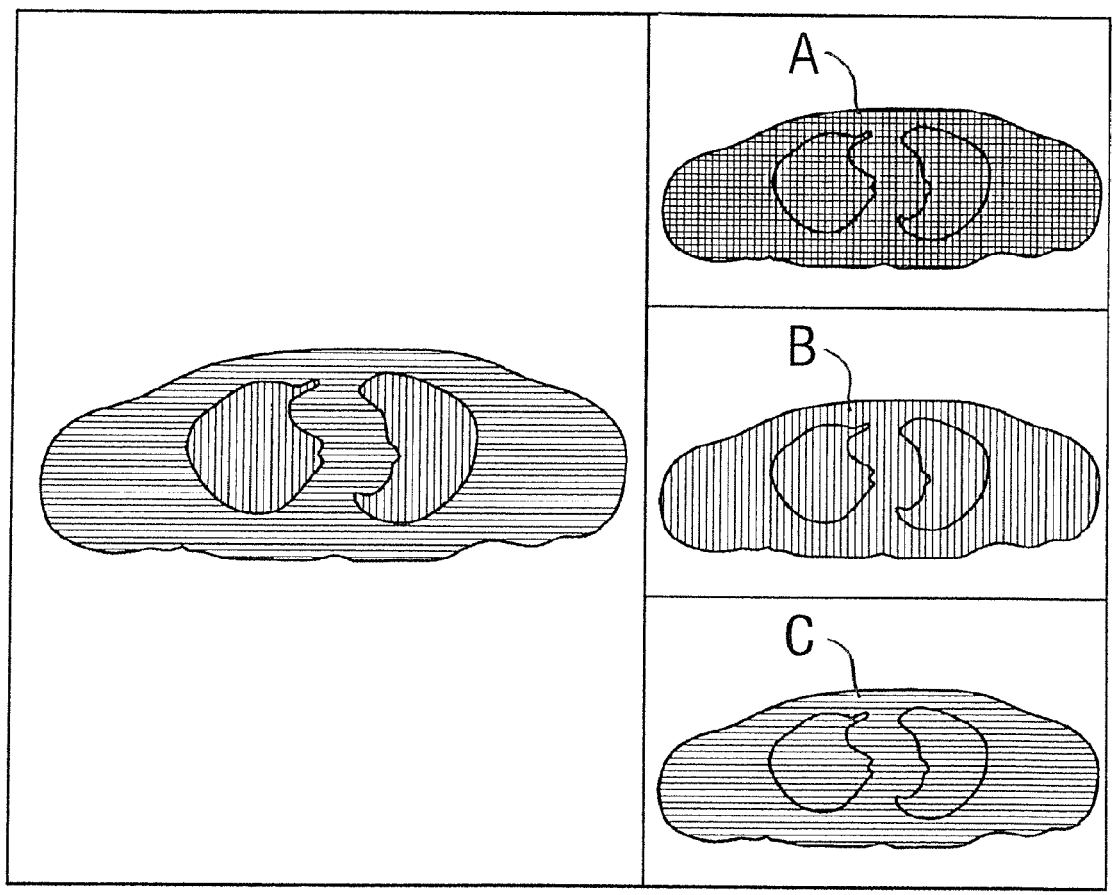
FIG. 2 shows an example of a fuses slice image displayed at a display screen together with respective slice images for different tracers.

FIG. 2 shows a possible realization of the invention similar to the combination of the representations shown in FIGS. 1A-1D. The displayed images in FIG. 2 are axial slices that are combined to form multi-fused slice image. The images shown in FIG. 2 are slices as derived from respective individual tracers A-C, made available for detailed examination. Preferably, that all four views are synchronized with each other such that the multi-fused slice image at the left in FIG. 2 always represents a combination of the slice images for tracers A, B and C.

The same applies to MIP rendering. The required different LUTs can be selected in such a way that the uptake of a particular tracer is either hidden or visualized in the combined MIP.

The present invention provides a method in which display properties of different image data sets are modified, based on anatomical location such that a combination of partial image data sets representing multiple tracers can be displayed in a single image. It does not directly provide highlighting of certain organs within an image.

In the case of multiple-tracers being combined in one study, so generating a single set of image data representing multiple tracers, the same concept can be utilized to compensate for the different uptake functions of the involved tracers in different organs/structures.

As an example, a tracer D may feature predominant uptake located inside the bones with a higher normal uptake than the other tracers. To improve the usefulness of, for example the MIP, the LUT may be adjusted for the bone regions in such a way that the average normal intensity is similar to the normal intensity in other structures/organs.

Manual adjustment of visualization parameters may be provided within the present invention.

Manual adjustment of window level: for conventional functional data displays, the user typically holds down a mouse button and moves the mouse left or right to adjust the bottom and up or down to adjust the top. This could be extended to this invention to consider the anatomical region in which the cursor was positioned prior to window level adjustment. For instance, following on from the above example, if the user depressed the mouse button whilst in the liver, only the window level for the liver (i.e., displaying tracer A) would be affected by the following movements of the mouse. Alternatively, if short cut keys are used to select a predefined window level, this change could be applied only to the anatomical region in which the mouse cursor, or cross-hair, or center of field of view as appropriate, is located.

Manual adjustment of LUT: for conventional functional data displays, a user typically changes the LUT by either selecting a different LUT from a menu such as a right-click menu or using short cut keys. As in the case of adjusting the window level, changes could be applied only to the anatomical region in which the mouse cursor or cross-hair, or center of field of view as appropriate is located. Beyond that, the user might want to toggle between different tracers for an organ of interest. For example, a short cut key may be utilized to toggle between different LUTs that visualize different tracers for a currently-selected anatomical region.

The visualization parameters on an organ and tracer basis can be stored to enhance the user's experience while toggling. Organ-specific workflows may be defined that store (default) settings for visualization parameters, such as windowing and zooming parameters, for single-tracer studies.

The above-described examples of the present invention do not conflict with the possibility of having global LUT/window combinations available for selection, either pre-defined or user-defined, or with adjusting visualization parameters such as windowing, globally as is conventional for single-tracer studies.

If the user wanted to create a clinical finding, for example defining a volume of interest VOI on the multi-tracer image such as FIG. 1D, the intensity values associated with that finding could be determined based on the functional image data being displayed in the region in which the finding was created. For example, if tracer A was dominant tracer displayed in the liver LUT and the user created a finding in the liver, it would be the intensity values from tracer A that would be displayed and reported for that finding. If desired by the user, corresponding values from the other tracers for this finding could also be displayed and reported.

The invention can be applied to any number of combinations of tracers for imaging systems such as PET/CT, SPECT/CT, SPECT/MR or MR/PET. The present invention may be applied for any combination of modalities, for example by utilizing color-coded LUTs and/or 3D visualization techniques such as MIPs. An example may be the use of different MRI diffusion/perfusion protocols as functional data on top of an anatomical T1/T2/PD-weighted scan or quantitative CT results on top of conventional anatomical data.

The present invention requires the alignment of the involved volumes (via hardware or software solutions) and a segmentation of the organs or structures of interest. This alignment may be performed automatically or semi-automatically by appropriate known methods, or may be performed manually. Such organs or structures include, but are not limited to, major organs such as lungs, liver, kidneys, brain, bladder, prostate, spleen, etc. or structures such as bone, muscles, fat, etc.

The described LUTs are specific to each combination of organ/structure and tracer and can be either pre-defined or adjustable by the user. LUTs may be adapted to automatically adjust for differences in dynamic range of the different tracers in different organs.

That is, each LUT, specific to a certain combination of organ/structure and tracer can be automatically adjusted based on data such as average tracer uptake within a VOI within the organ to align the dynamic range so that the visual brightness of the displayed volume is consistent throughout the volume.

The present invention may include use of LUTs that combine uptake measurements from multiple tracers, as an alternative to defining respective LUTs to show uptake from a single functional image alone.

One embodiment of an aspect of the invention is an apparatus for combining a plurality of image data sets into one multi-fused image for display to a user, comprising: a processor adapted to align all image data sets with a data set representing corresponding anatomical data; segment the image data in each data set into separate regions representing respective structures of interest by reference to a segmentation derived from anatomical data; for each region, select a corresponding segment of image data from a selected image data set; and combine the selected segments of the image data set to generate a multi-fused image of the regions, including the steps of applying spatially dependent look-up tables to the plurality of image data sets, thereby to determine whether each data set is hidden or displayed for each region; and a display device adapted to display the multi-fused image of the regions.

One embodiment of an aspect of the invention is a media device storing computer program code adapted, when loaded into or run on a computer, to cause the computer to become apparatus, or to carry out a method, according to any of the above embodiments.

Referring to FIG. 3, the above embodiments of the invention may be conveniently realized as a computer system suitably programmed with instructions for carrying out the steps of the methods according to the invention.

For example, a central processing unit 4 is able to receive data representative of medical scan data via a port 5 which could be a reader for portable data storage media (e.g. CD-ROM); a direct link with apparatus such as a medical scanner (not shown) or a connection to a network.

For example, in an embodiment, the processor performs such steps as (a) aligning all image data sets with a data set representing corresponding anatomical data;

(b) segmenting the image data in each data set into separate regions representing respective structures of interest by reference to a segmentation derived from anatomical data;

(c) for each region, selecting a corresponding segment of image data from a selected image data set; and (d) combining the selected segments of the image data set to generate the multi-fused image of the regions, including the steps of applying spatially dependent look-up tables to the plurality of image data sets, thereby to determine whether each data set is hidden or displayed for each region.

Software applications loaded on memory 6 are executed to process the image data in random access memory 7.

A Man-Machine interface 8 typically includes a keyboard/mouse/screen combination (which allows user input such as initiation of applications) and a screen on which the results of executing the applications are displayed.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for combining a plurality of segmented images into one multi-fused image for display to a user, comprising:
   providing a processor with a plurality of sets of functional image data, each acquired from a subject using a different tracer, selected from the group consisting of an individual tracer and a combination of tracers;
   in said processor, reconstructing a respective image from each of said sets of functional image data, each of said images showing a respectively different anatomical structure of interest of the subject resulting from the respective tracer used to produce the respective set of functional image data from which the respective image is reconstructed, but not showing respective anatomical structures of interest of the subject resulting from others of said tracers;
   in said processor, applying a segmentation algorithm to each of said images that segments the respective anatomical structure of interest in each of said images;
   in said processor, accessing electronically stored tracer-dependent look up tables that each represent a spatial dependency of one of said tracers;
   in said processor, respectively applying the tracer-dependent look up tables to the respective segmented anatomical structures of interest to produce, for each segmented anatomical structure of interest, a displayable version thereof wherein a visual appearance of the respective segmented anatomical structure of interest is adapted to the respective tracer thereof;
   in said processor, fusing the respective displayable versions of the respective anatomical structures of interest into one multi-fused image of the subject; and
   displaying said one multi-fused image of the subject at a display in communication with said processor.

2. A method according to claim 1 wherein one or more of the images is displayed at a display screen alongside the multi-fused image.

3. A method according to claim 2 wherein the images displayed at said display screen are synchronized with the multi-fused image displayed at said display screen.

4. A method according to claim 1 wherein, for each selected segment, one or more display parameters are adjusted to optimize said visual appearance of each segment in each displayable version in said multi-fused image.

5. A method according to claim 1 wherein at least some of the structures correspond to organs of the subject.

6. A method according to claim 1 wherein said segments are differently colored in the multi-fused image.

7. A method according to claim 1 wherein the look-up tables are automatically adjusted to align a dynamic range of each selected segment to compensate for differences in uptake of respective tracers among said different tracers.

8. A method according to claim 1 wherein the application of the look-up tables promotes visual differentiation between the uptake of respective tracers of said segments.

9. A method according to claim 1 wherein the plurality sets of functional image data are acquired simultaneously.

10. An apparatus method for combining a plurality of segmented images into one multi-fused image for display to a user, comprising:

a processor provided with a plurality of sets of functional image data, each acquired from a subject using a different tracer, selected from the group consisting of an individual tracer and a combination of tracers;

said processor being configured to reconstruct a respective image from each of said sets of functional image data, each of said images showing a respectively different anatomical structure of interest of the subject resulting from the respective tracer used to produce the respective set of functional image data from which the respective image is reconstructed, but not showing respective anatomical structures of interest of the subject resulting from others of said tracers;

said processor being configured to apply a segmentation algorithm to each of said images that segments the respective anatomical structure of interest in each of said images;

a memory in which tracer-dependent look up tables are stored that each represent a spatial dependency of one of said tracers;

said processor being configured to access said memory and respectively apply the tracer-dependent look up tables to the respective segmented anatomical structures of interest to produce, for each segmented anatomical structure of interest, a displayable version thereof wherein a visual appearance of the respective segmented anatomical structure of interest is adapted to the respective tracer thereof;

said processor being configured to fuse the respective displayable versions of the respective anatomical structures of interest into one multi-fused image of the subject;

a display monitor in communication with said processor; and said processor being configured to display said one multi-fused image of the subject at said display monitor.

11. A non-transitory, computer-readable data storage medium encoded with programming instructions, said storage medium being loaded into a processor, and said programming instructions causing said processor to:

receive a plurality of sets of functional image data, each acquired from a subject using a different tracer, selected from the group consisting of an individual tracer and a combination of tracers;

reconstruct a respective image from each of said sets of functional image data, each of said images showing a respectively different anatomical structure of interest of the subject resulting from the respective tracer used to produce the respective set of functional image data from which the respective image is reconstructed, but not showing respective anatomical structures of interest of the subject resulting from others of said tracers;

apply a segmentation algorithm to each of said images that segments the respective anatomical structure of interest in each of said images;

access electronically stored tracer-dependent look up tables that each represent a spatial dependency of one of said tracers;

respectively apply the tracer-dependent look up tables to the respective segmented anatomical structures of interest to produce, for each segmented anatomical structure of interest, a displayable version thereof wherein a visual appearance of the respective segmented anatomical structure of interest is adapted to the respective tracer thereof;

fuse the respective displayable versions of the respective anatomical structures of interest into one multi-fused image of the subject; and display said one multi-fused image of the subject at a display in communication with said processor.

* * * * *